(12) United States Patent
Hu et al.

(10) Patent No.: US 11,674,122 B2
(45) Date of Patent: Jun. 13, 2023

(54) METHOD FOR INDUCING DIFFERENTIATED CELL INTO MESENCHYMAL STEM CELL, AND COMBINATIONS OF REGULATORY TARGETS THEREOF

(71) Applicant: Yunnan Jici Institute for Regenerative Medicine Co., Ltd., Kunming (CN)

(72) Inventors: Min Hu, Kunming (CN); Yanjiao Li, Kunming (CN)

(73) Assignee: Yunnan Jici Institute for Regenerative Medicine Co., Ltd., Kunming (CN)

( * ) Notice: Subject to any disclaimer, the term of this patent is extended or adjusted under 35 U.S.C. 154(b) by 905 days.

(21) Appl. No.: 16/347,627

(22) PCT Filed: Nov. 6, 2017

(86) PCT No.: PCT/CN2017/109488
§ 371 (c)(1),
(2) Date: May 6, 2019

(87) PCT Pub. No.: WO2018/082690
PCT Pub. Date: May 11, 2018

(65) Prior Publication Data
US 2019/0345451 A1    Nov. 14, 2019

(30) Foreign Application Priority Data
Nov. 7, 2016 (CN) .......................... 201610975744.4

(51) Int. Cl.
*C12N 5/0775* (2010.01)
(52) U.S. Cl.
CPC ........ *C12N 5/0663* (2013.01); *C12N 2501/01* (2013.01); *C12N 2501/15* (2013.01); *C12N 2501/415* (2013.01); *C12N 2501/727* (2013.01); *C12N 2501/999* (2013.01); *C12N 2506/09* (2013.01); *C12N 2506/11* (2013.01); *C12N 2506/13* (2013.01); *C12N 2506/1307* (2013.01)
(58) Field of Classification Search
CPC .......................... C12N 5/0663; C12N 2506/13
See application file for complete search history.

(56) References Cited

FOREIGN PATENT DOCUMENTS

| CN | 104894060 A | 9/2015 |
|---|---|---|
| CN | 105441384 A | 3/2016 |
| CN | 105861428 A | 8/2016 |
| WO | 2016081032 A2 | 5/2016 |
| WO | 2016148253 A1 | 9/2016 |

OTHER PUBLICATIONS

LeBleu, The FASEB Journal, 2020, 34:3519-3536.*
Huang, Biochemistry, 2014, 53:5737-5749.*
Black, 2013, Frontiers in Immunology, 3:423, pp. 1-17.*
Yan, 2016, Molecular Medicine Reports, 13:3715-3723.*
Heldin, 2016, CSH Perspectives in Biology, 8:1-34.*
MacDonald (2009, Developmental Cell, 17:9-26).*
Katoh, Cancer Biology and Therapy, 2006, 5:1059-1064.*
Willert, CSH Perspectives in Biology, 2012, 4:1-13.*
Thoma E.C., et al. Chemical Conversion of Human Fibroblasts into Functional Schwann Cells. Stem Cell Reports. Oct. 14, 2014. vol. 3, pp. 539-547.
Hu Wenxiang, et al. Direct Conversion of Normal and Alzheimer's Disease Human Fibroblasts into Neuronal Cells by Small Molecules. Cell Stem Cell 17. Aug. 6, 2015, pp. 204-212.
Saiyong Zhu, Sheng Ding et al. Human Pancreatic Beta-Like Cells Converted from Fibroblasts. Nature Communications. Jan. 6, 2016, 7:10080 DOI: 10.1038/ncomms10080.

* cited by examiner

*Primary Examiner* — Valarie E Bertoglio
(74) *Attorney, Agent, or Firm* — Bayramoglu Law Offices LLC

(57) ABSTRACT

A method for inducing differentiated cells into mesenchymal stem cells (MSCs), and combinations of regulatory targets thereof. The method includes performing a directional induction on the differentiated cells to prepare the mesenchymal stem cells. The directional induction includes treating cells by inhibiting the TGF-β signal pathway, inhibiting the activity of PKC, activating the WNT/β-catenin signal pathway and activating the cAMP signal pathway. By regulating corresponding signal pathways and/or enzymatic activities by stages, the differentiated cells are induced into the mesenchymal stem cells.

6 Claims, 4 Drawing Sheets

METHOD FOR INDUCING DIFFERENTIATED CELL INTO MESENCHYMAL STEM CELL, AND COMBINATIONS OF REGULATORY TARGETS THEREOF

CROSS REFERENCE TO THE RELATED APPLICATIONS

This application is the national phase entry of International Application No. PCT/CN2017/109488, filed on Nov. 6, 2017, which is based upon and claims priority to Chinese Patent Application No. 201610975744.4, filed on Nov. 7, 22016, the entire contents of which are incorporated herein by reference.

TECHNICAL FIELD

The present invention relates to the fields of cell biology, tissue engineering and regenerative medicine, and particularly to a method for inducing differentiated cells into mesenchymal stem cells, and combinations of regulatory targets thereof.

BACKGROUND

Mesenchymal Stem Cells (MSCs) are a kind of adult stem cells with multiple differentiation potential, which widely exist in human bone marrow, fat and peripheral blood. Compared with embryonic stem cells or induced pluripotent stem cells (iPSCs), MSCs have higher safety, stability and lower immunogenicity. MSCs have been applied in clinical research and treatment of bone and joint injury, cancer, liver cirrhosis, diabetes mellitus, degenerative diseases, nerve injury, senile dementia and lupus erythematosus, showing great industrial value. However, MSCs have not been widely used due to the concerns about their rare number, limited source, difficulty in enrichment, complexity of acquisition process, restriction of donor health status, aging, and difficulty in expansion in a large number. Embryonic stem cells and iPSCs can be differentiated into mesenchymal stem cells, but they have not been widely used because of ethical problems or safety risks.

At present, functional somatic cells of other lineage, such as muscle cells, neurons, stem cells, etc., could be obtained from a type of differentiated cell, such as skin fibroblasts, by cell transdifferentiation technologies. Among them, the direct transdifferentiation technologies using small molecule compounds and combinations thereof have the following characteristics: (1) no introduction of exogenous transcription factors, no change in the genetic structure of the source cells, good safety and stability, and no immunogenicity; (2) the induction system is stable, easy to control and economic; and (3) the induction process is short, highly efficient, and easy for high scale production. Therefore, it is expected to become a basic technology for the development and production of seed cells for regenerative medicine.

Traditional methods for cell transdifferentiation require the introduction of specific exogenous genes, sometimes accompanied by synergistic action of small molecule compounds or signaling molecules. There are many reports focused on inducing one type of differentiated cell to another functionally differentiated cell by introducing exogenous genes. For example, it has been reported that exogenous genes of BMP-2, BMP-7 and LMP-3 can independently or synergistically transdifferentiate skin fibroblasts into osteoblasts having bone formation function in vitro and in vivo. However, the introduction of exogenous genes has the risk of tumorigenesis and may cause the target cells to be immunogenic, which is difficult for application. In 2013, Hongkui DENG reported that mouse skin fibroblasts could be reprogrammed into neurons only using small molecule compounds or combinations thereof and confirmed that the cell differentiation technology has the advantages of having short induction process, stable induction system, easy quality control, low cost, no tumorigenic risk caused by insertion of exogenous gene, and the obtained target cells have good safety and stability and no immunogenicity, possessing potential clinical application value and industrial prospects. Thereafter, the Chinese patent Application (Application No. 201410075246.5) provides a method for inducing differentiated cells into neural stem cells and an application thereof. Specifically, this Application is to use a combination of histone deacetylases (HDACs) inhibitors, glycogen synthase kinase (GSK-3) inhibitors and transforming growth factor beta (TGF-$\beta$) signaling pathway inhibitors to induce differentiated cells, such as fibroblasts and epithelial cells, into neural stem cells with good multipotency and passaging stability under hypoxia condition. The Chinese patent Application (Application No. 20160213644.8) provides an induction medium for inducing fibroblasts into cardiomyocytes, a method and an application thereof. The induction medium includes basic medium and small molecule combinations. The said small molecule combinations are 6TCFOW or SCFOV, of which 6 is E615 41, T is amphetamine, C is CHIR99021, F is forskolin, O is Dorsomorphin, W is IWR-1, S is SB431542 and V is valproic acid. The induction medium of this Application can induce fibroblasts into cardiomyocytes. At present, it's reported that Schwann cells (THOMA E C, et al, 2014), nerve cells (HU W, et al, 2015) and islet cells (Sheng Ding, et al, 2015) have been obtained from human differentiated cells such as skin fibroblasts by using simple small molecule compounds or their combinations.

Because there are about 25% genetic differences between human and mice, the technical solutions of the above-mentioned patent applications which have been successfully applied in mouse cell reprogramming are not feasible in the human cell reprogramming. Moreover, due to the induction mechanism and technical means for using the same types of cells to obtain different target cells through transdifferentiation are different, other types of target cells which have not been reported cannot be obtained by adopting the above technical solutions. Applicant repeated the trials in humans using the above reported technical solutions respectively, failing to successfully apply the reprogramming technique applied to mouse cells to the reprogramming of the same type of cells in human and failing to induce human differentiated cells into mesenchymal stem cells. Various differentiated cells, such as skin fibroblasts, have the advantages of having abundant sources, being easy to obtain and easy to be proliferated and cultured in vitro. At present, cell transdifferentiation technology has been used to directly induce differentiated cells such as skin fibroblasts into myoblasts, neurons, hepatocytes, osteoblasts, etc., or used to induce the differentiated cells into pluripotent stem cells first, and then the pluripotent stem cells can be further introduced into corresponding functional cells. The above functional cells obtained by direct or indirect induction from a specific differentiated cells such as skin fibroblasts by cell transdifferentiation technology no longer maintain the molecular characteristics and functions of the source cells, but obtain the typical molecular characteristics and functions of the target cells. Nowadays, the above induced functional cells have been gradually applied in disease model research, clinical treatment research and tissue engineering research.

Traditional methods for cell transdifferentiation require the introduction of specific exogenous genes, sometimes accompanied by synergistic action of small molecule compounds or signaling molecules. There are many reports focused on inducing one type of differentiated cell to another functionally differentiated cell by introducing exogenous genes. For example, it has been reported that exogenous genes of BMP-2, BMP-7 and LMP-3 can independently or synergistically transdifferentiate skin fibroblasts into osteoblasts having bone formation function in vitro and in vivo. However, the introduction of exogenous genes has the risk of tumorigenesis and may cause the target cells to be immunogenic, which is difficult for application. In 2013, Hongkui DENG reported that mouse skin fibroblasts could be reprogrammed into neurons only using small molecule compounds or combinations thereof and confirmed that the cell differentiation technology has the advantages of having short induction process, stable induction system, easy quality control, low cost, no tumorigenic risk caused by insertion of exogenous gene, and the obtained target cells have good safety and stability and no immunogenicity, possessing potential clinical application value and industrial prospects. Thereafter, the Chinese patent Application (Application No. 201410075246.5) provides a method for inducing differentiated cells into neural stem cells and an application thereof. Specifically, this Application is to use a combination of histone deacetylases (HDACs) inhibitors, glycogen synthase kinase (GSK-3) inhibitors and transforming growth factor beta (TGF-β) signaling pathway inhibitors to induce differentiated cells, such as fibroblasts and epithelial cells, into neural stem cells with good multipotency and passaging stability under hypoxia condition. The Chinese patent Application (Application No. 20160213644.8) provides an induction medium for inducing fibroblasts into cardiomyocytes, a method and an application thereof. The induction medium includes basic medium and small molecule combinations. The said small molecule combinations are 6TCFOW or SCFOV, of which 6 is E615 41, T is amphetamine, C is CHIR99021, F is forskolin, O is Dorsomorphin, W is IWR-1, S is SB431542 and V is valproic acid. The induction medium of this Application can induce fibroblasts into cardiomyocytes. At present, it's reported that Schwann cells (THOMA E C, et al, 2014), nerve cells (HU W, et al, 2015) and islet cells (Sheng Ding, et al, 2015) have been obtained from human differentiated cells such as skin fibroblasts by using simple small molecule compounds or their combinations.

Because there are about 25% genetic differences between human and mice, the technical solutions of the above-mentioned patent application which have been successfully applied in mouse cell reprogramming are not feasible in the human cell reprogramming. Moreover, due to the induction mechanism and technical means for using homogeneous cells to obtain different target cells through transdifferentiation are different, other types of differentiated cells which have not been reported cannot be obtained by adopting the above technical solutions. Applicant has repeated the trials in human using the above reported technical solutions respectively, failing to successfully apply the reprogramming technique applied to mouse cells to the reprogramming of the same type of cells in human and failing to induce human differentiated cells into mesenchymal stem cells.

SUMMARY

The present invention provides a method for inducing differentiated cells into mesenchymal stem cells, and combinations of regulatory targets thereof. According to the present invention, a large number of induced mesenchymal stem cells or products thereof are obtained rapidly, stably and programmatically by treating differentiated cells using a combination of small molecule compounds in a timely phased processing manner.

In the first aspect of the present invention, a method for inducing differentiated cells into mesenchymal stem cells is provided. The method includes performing a directional induction on the differentiated cells to prepare mesenchymal stem cells. The directional induction includes inhibiting the TGF-β signal pathway, inhibiting the activity of PKC, activating the WNT/β-catenin signal pathway and activating the cAMP signal pathway.

The directional induction also includes activating the RA signal pathway and/or inhibiting the activity of DNMT and/or inhibiting the activity of HMT and/or inhibiting the activity of histone demethylases, and/or inhibiting the JNK signal pathway and/or inhibiting ROCK signal pathway and/or inhibiting the activity of lysine deacetylases to finally prepare the mesenchymal stem cells.

Pretreatment of the differentiated cells before the directional induction includes inhibition of TGF-β signaling pathway, activation of WNT/β-catenin signaling pathway and activation of cAMP signaling pathway; or the pretreatment includes inhibition of the activity of Lysine deacetylases inhibitors (KDACIs), inhibition of TGF-β signaling pathway, activation of WNT/β-catenin signaling pathway and activation cAMP signaling pathway.

Further, adding ascorbic acid and/or growth factor BMP4 and/or PDGF-AB and/or basic fibroblast growth factor b-FGF to contact cells or cell products during the directional induction process to increase the induction efficiency.

Further, the signaling pathway of TGF-β refers specifically to the signaling pathway in which type I TGF-β receptor is participated, and the signaling pathway of cAMP is EPAC/RAP1 signaling pathway.

The differentiated cells contact with a combination of small molecule compounds to regulate the corresponding signaling pathways (such as cAMP, TGF-β, WNT/β-catenin, JNK, ROCK, RA signaling pathways, etc.) and/or enzymes (such as DNMT, HMT, PKC and lysine deacetylases, etc.).

The differentiated cell is pretreated for about 3-10 days to obtain a first treated cell, and the first treated cell is directionally induced for another 2-20 days using TGF-β signaling pathway inhibitor, PKC signaling pathway inhibitor, WNT/β-catenin signaling pathway activator and cAMP signaling pathway activator; or the first treated cell is directionally induced using at least one of TGF-β signaling pathway inhibitor, PKC inhibitor, WNT/β-catenin signaling pathway activators, cAMP signaling pathway activators, RA signaling pathway activators, DNMT inhibitors, HMT inhibitors, histone demethylases inhibitors, JNK signaling pathway inhibitors, ROCK signaling pathway inhibitors and lysine deacetylases inhibitors for another 2-20 days.

The differentiated cells are derived from mammals such as human beings, and the differentiated cells include fibroblasts, epithelial cells, adipocytes or blood cells. Preferably, the differentiated cells are fibroblasts.

In the second aspect of the present invention, induced mesenchymal stem cells prepared by the method are provided. In the implementation solutions of the present invention, the mesenchymal stem cells have the characteristics of natural mesenchymal stem cells; and the induced mesenchymal stem cells can be expanded by trillions of times with large quantities and high purity, and have good industrialization prospects.

The induced mesenchymal stem cells obtained by the method of the present invention have good performance in multiple differentiation potential to multiple germ-layer cells, stably passaging, high efficiency for expansion. The preparation process is operated in stages timely, which is convenient for precise operation, systematic quality control, scaled and standardized production. The present invention provides a large number of mesenchymal stem cells specifically or individually without limitation of donor sources, which is expected to be developed into models, technologies or drugs for basic research or clinical treatment of diseases such as bone and joint injuries, cancer, liver cirrhosis, diabetes, degenerative diseases, nerve injury, senile dementia and lupus erythematosus.

In the third aspect of the present invention, an application of the induced mesenchymal stem cells and products thereof are provided. The induced mesenchymal stem cells and products thereof can be used for basic research, clinical treatment, tissue engineering product development and production, and preparing a combination of small molecular compounds to prepare the mesenchymal stem cells.

In the fourth aspect of the present invention, a combination of regulatory targets for regulating the above-mentioned signaling pathways and/or enzymatic activities are provided. The regulatory targets include at least one of TGF-β receptors, PKC, WNT/β-catenin, cAMP, JNK, ROCK, DNMT, HMT, lysine deacetylases and histone demethylases.

The combination of the regulatory targets includes inhibiting the TGF-β signaling pathway, inhibiting the PKC activity, activating the WNT/β-catenin signaling pathway and activating the cAMP signaling pathway.

The combination of the regulatory targets further includes activating the signal pathway of RA and/or inhibiting the activity of DNMT and/or inhibiting the activity of EMT and/or inhibiting the activity of histone demethylases and/or inhibiting the signal pathway of JNK and/or inhibiting the signal pathway of ROCK and/or inhibiting lysine deacetylases.

The combination of the regulatory targets works in stages according to time sequence. The first stage is: inhibiting the TGF-β signal pathway, activating the WNT/β-catenin signal pathway and activating the cAMP signal pathway; or the first stage is: inhibiting the activity of Lysine deacetylases inhibitors (KDACIs), inhibiting the signal pathway of TGF-β, activating the signal pathway of WNT/β-catenin and activating the cAMP signaling pathway.

The second stage is: inhibiting the TGF-β signaling pathway, inhibiting the activity of PKC, activating WNT/β-catenin signaling pathway and activating the cAMP signaling pathway; or the second stage is: inhibiting the TGF-β signaling pathway, inhibiting the activity of PKC, activating the WNT/β-catenin signaling pathway and activating the cAMP signaling pathway, and simultaneously activating the RA signaling pathway and/or inhibiting the activity of DNMT and/or inhibiting the activity of EMT and/or inhibiting the activity of histone demethylases and/or inhibiting the JNK signaling pathway and/or inhibiting the ROCK signaling pathway and/or inhibiting the lysine deacetylases activity.

In the fifth aspect of the present invention, a combination of small molecule compounds acting on the above regulatory targets are provided, and different small molecule compounds act on their respective regulatory targets.

In the sixth aspect of the present invention, an application of the combination of regulatory targets or the combination of small molecule compounds in cell reprogramming is provided. The combinations are applied to mobilize and/or induce mesenchymal stem cells in vivo or in vitro or other regenerative medical seed cells, tissue engineering seed cells (such as hepatocytes, osteoblasts, chondrocytes, etc.) and products thereof derived from the induced mesenchymal stem cells in vivo or in vitro, which can be used for basic research, clinical treatment and tissue engineering products research and production.

The method of the present invention is carried out under conditions suitable for the production of induced mesenchymal stem cells, including, for example, the composition and concentration of the culture medium, the culture temperature, the culture time and other conditions. Based on the sufficient instruction of the prior art and the enumerated embodiments of the present invention, the above-mentioned inducing conditions can be easily determined by the skilled personnel in the art without excessive experiments. The key in the present invention is to select the cell signaling pathways that need to be inhibited or activated, and to determine the order in which the cell signaling pathways act. In addition, the concentration and other conditions of small molecule compounds or combinations thereof could also be adapted on the basis of the scope of the present invention.

The mechanism of the present invention is as follows: the differentiated cells are dedifferentiated and reprogrammed into the mesenchymal stem cells by the treatment of histone acetylation and methylation, the activation of endogenous transcription factors of reprogramming, and the synergistic effects of inhibiting TGF-β signaling pathway, activating WNT/β-catenin signaling pathway, activating cAMP signaling pathway, activating RA signaling pathway and inhibiting PKC activity and so on.

The combination of small molecule compounds of the present invention includes the following components: TGF-β signaling pathway inhibitor, WNT/β-catenin signaling pathway agonist, cAMP signaling pathway agonist and PKC inhibitor.

Further, the combination of small molecular compounds also includes at least one of RA signaling pathway agonists, DNMT inhibitors, EMT inhibitors, histone demethylases inhibitors, ascorbate, JNK signaling pathway inhibitors, ROCK signaling pathway inhibitors and lysine deacetylases inhibitors.

Preferably, the combination of small molecule compounds includes a first stage contact activation component and a second stage contact induction component in a time sequence. The first stage contact activation component includes at least two of TGF-β signaling pathway inhibitor, WNT/β-catenin signaling pathway agonist and cAMP signaling pathway agonist; and the second stage contact induction component includes TGF-β signaling pathway inhibitor, WNT/β-catenin signaling pathway agonist, cAMP signaling pathway agonist and PKC inhibitor.

Further, the first stage contact activation component includes at least two of lysine deacetylases inhibitors, TGF-β signaling pathway inhibitors, WNT/β-catenin signaling pathway agonists and cAMP signaling pathway agonists; the second stage contact induction component further includes at least one of RA signaling pathway agonists, DNMT inhibitors, EMT inhibitors, histone demethylases inhibitors, ascorbate, JNK signaling pathway inhibitors, ROCK signaling pathway inhibitors and lysine deacetylases inhibitors.

Further, the TGF-β signaling pathway is a signaling pathway in which the type I TGF-β receptor participates; and the cAMP signaling pathway is an EPAC/RAP1 signaling pathway.

The lysine deacetylases inhibitors include at least one of the following molecules: sodium phenyl butyrate, butyrate, sodium butyrate, MC1568, CI994 (Tacedinaline), chidamide, CAY10683 (SantacruzaMate A), CUDC-907, M344 (Histone Deacetylase Inhibitor III), LAQ824 (NVP-LAQ824, Dacinostat), Pracinostat (SB939), VPA, Scriptaid, Apicidin, LBH-589 (Panobinostat), MS-275, SAHA (Vorinostat), Trichostatin (TSA), Psammaplin A, PCI-24781 (Abexinostat), Rocilinostat (ACY-1215), Mocetinostat (MGCD0103), 4-Phenylbutyrate (4PB), splitomicin, SRT1720, resveratrol, Sirtinol, APHA, CI-994, Depudecin, FK-228, HC-Toxin, ITF-2357 (Givinostat), Chidamide, RGFP 966, PHOB, BG45, Nexturastat A, TMP269, CAY10603, MGCD-0103, Niltubacin, PXD-101 (Belinostat), Pyroxamide, Tubacin, EX-527, BATCP, Cambinol, MOCPAC, PTACH, MC1568, NCH51 and TC-H106.

The TGF-β receptor inhibitors include at least one of 616452, LY2109761, Pirfenidone, Repsox (E-616452), SB431542, A77-01, Tranilast, Galunisertib (LY2157299), A8301, GW788388, ITD-1, SD208, SB525334, LY364947, ASP3029, D4476 and SB505124.

The PKC inhibitors include at least one of Go6983, Ro31-8220 Mesylate, Go6976 and Bisindolylmaleimide I (GF109203X).

The WNT/β-catenin signaling pathway agonists include at least one of MAY-262611, CHIR98014, CHIR99021, LiCl, Li2CO3, TD114-2, AZD2858, AZD1080, BIO, Kenpaullone, TWS119, LY2090314, CBM1078, SB216763 and AR-A014418.

The cAMP agonists include at least one of EPAC/RAP1 agonists, 8-Bromo-cAMP, Dibutyryl-Camp and SP-8-Br-cAMPs.

The EPAC/RAP1 agonists include at least one of Forskolin, IBMX, Prostaglandin E2 (PGE2), NKH477, 8-pCPT-2'-O-Me-cAMP, GSK256066, Apremilast (CC-10004) Roflumilast, Cilomilast, Rolipram and Milrinone.

The RA signaling pathway agonists include at least one of TTNPB, Bexarotene, Ch55, Tamibarotene, Retinol, AM580, ATRA, 13-cis RA, Vitamin A and Vitamin A derivatives.

ROCK inhibitors include at least one of Y-27632, Y-27632 2HCl, Thiazovivin, Ripasudil (K-115), Fasudil, Fasudil (HA-1077) HCl, GSK429286A, RKI-1447 and PKI-1313.

The JNK inhibitors include at least one of SP600125, JNK Inhibitor IX, AS601245, AS602801 and JNK-IN-8.

The DNMT inhibitors include at least one of RG108, Thioguanine, 5-Aza-2'-deoxycytidine (Decitabine), SGI-1027, Zebularine, and 5-Azacytidine (AZA).

The HMT inhibitors include at least one of EPZ004777, EPZ5676, GSK503, BIX 01294 and SGC 0946.

The histone demethylases inhibitors include at least one of parnate (tranylcypromine), Tranylcypromine (2-PCPA) HCl SP2509, 4SC-202, ORY-1001 (RG-6016), GSKJ1 and GSK-LSD1.

As an optimization, the combination of small molecular compounds is any one of the following:
VPA+CHIR99021+Repsox+Forskolin+Go6983;
VPA+CHIR99021+SB431542+Forskolin+Go6983;
BIO+SB431542+Forskolin+Go6983;
CHIR99021+Repsox+Forskolin+Go6983+Rolipram;
CHIR99021+Repsox+Forskolin+Go6983+Rolipram+SB431542;
CHIR99021+SB431542+Forskolin+Go6983+Rolipram;
BIO+SB431542+Forskolin+Go6983+Rolipram;
VPA+CHIR99021+Repsox+Forskolin+Go6983+NaB;
CHIR99021+Repsox+Forskolin+Go6983+NaB;
VPA+BIO+SB431542+Rolipram+Go6983;
BIO+SB431542+Rolipram+SP600125+Go6983;
VPA+BIO+SB431542+Forskolin+Go6983;
VPA+CHIR99021+SB431542+Rolipram+Go6983;
VPA+CHIR99021+Repsox+Forskolin+Go6983+SP600125;
VPA+CHIR99021+Repsox+Forskolin+Go6983+8-pCPT-2'-O-Me-cAMP;
VPA+CHIR99021+Repsox+Forskolin+Go6983+SB431542;
VPA+CHIR99021+SB431542+Forskolin+Go6983+Tranilast;
VPA+CHIR99021+Repsox+Forskolin+Go6983+SB431542+A8301;
VPA+CHIR99021+Repsox+Forskolin+Go6983+Rolipram+SB431542+A8301;
VPA+CHIR99021+Repsox+Forskolin+Go6983+Rolipram+SB431542;
VPA+CHIR99021+Repsox+Forskolin+Go6983+SP600125+Parnate;
VPA+CHIR99021+Repsox+Forskolin+Go6983+Rolipram;
VPA+CHIR99021+Repsox+Forskolin+Go6983+Rolipram+SB431542;
VPA+CHIR99021+Repsox+Rolipram+Go6983;
VPA+CHIR99021+Repsox+Forskolin+Go6983+Parnate;
VPA+BIO+Repsox+Forskolin+Go6983;
CHIR99021+Repsox+Forskolin+Go6983;
CHIR99021+Repsox+Rolipram+Go6983;
CHIR99021+SB431542+Forskolin+Go6983;
CHIR99021+SB431542+Rolipram+Go6983;
CHIR99021+Repsox+Forskolin+SP600125+Go6983;
CHIR99021+Repsox+Forskolin+SP600125+Parnate+Go6983;
BIO+Repsox+Forskolin+Go6983+Rolipram;
BIO+Repsox+Forskolin+Go6983;
BIO+Repsox+Forskolin+Go6983+SP600125;
BIO+SB431542+Rolipram+Go6983;
BIO+SB431542+Rolipram+Go6983+SP600125;
BIO+SB431542+Rolipram+Go6983+SP600125+Parnate;
VPA+BIO+SB431542+Rolipram+Go6983+SP600125;
VPA+CHIR99021+Repsox+Forskolin+Go6983+5-Aza-2'-deoxycytidine;
VPA+CHIR99021+Repsox+Forskolin+Go6983+SP600125+5-Aza-2'-deoxycytidine;
VPA+CHIR99021+Repsox+Forskolin+Go6983+TTNPB+EPZ004777;
VPA+CHIR99021+Repsox+Forskolin+Go6983+TTNPB+EPZ004777+AM580;
VPA+CHIR99021+Repsox+Forskolin+Go6983+TTNPB+EPZ004777+5-Aza-2'-deoxycytidine;
VPA+CHIR99021+Repsox+Forskolin+Go6983+TTNPB+EPZ004777+AM580+5-Aza-2'-deoxycytidine;
VPA+CHIR99021+Repsox+Forskolin+Go6983+TTNPB+EPZ004777+5-Aza-2'-deoxycytidine+SP600125;
VPA+CHIR99021+Repsox+Forskolin+Go6983+TTNPB+EPZ004777+5-Aza-2'-deoxycytidine+SP600125+AM580;
VPA+CHIR99021+Repsox+Forskolin+Go6983+TTNPB+EPZ004777+SP600125;
VPA+CHIR99021+Repsox+Forskolin+Go6983+TTNPB+EPZ004777+AM580+SP600125
VPA+CHIR99021+Repsox+Forskolin+Go6983+TTNPB+EPZ004777+AM580+SP600125+Y27632;
VPA+CHIR99021+Repsox+Forskolin+Go6983+TTNPB+EPZ004777+AM580+SP600125+Y27632+5-Aza-2'-deoxycytidine;

VPA+CHIR99021+Repsox+Forskolin+Go6983+
TTNPB+EPZ004777+AM580+SP600125+Y27632+5-Aza-
2'-deoxycytidine+ascorbate;
VPA+CHIR99021+Repsox+Forskolin+Go6983+
TTNPB+EPZ004777+AM580+SP600125+Y27632+ascorbate;
VPA+CHIR99021+Repsox+Forskolin+Go6983+
TTNPB+EPZ004777+AM580+Y27632+ascorbate;
VPA+CHIR99021+Repsox+Forskolin+Go6983+
TTNPB+EPZ004777+AM580+Y27632+ascorbate+5-Aza-
2'-deoxycytidine;
VPA+CHIR99021+Repsox+Forskolin+Go6983+
TTNPB+EPZ004777+Parnate;
VPA+CHIR99021+Repsox+Forskolin+Go6983+
TTNPB+EPZ004777+AM580+Parnate;
VPA+CHIR99021+Repsox+Forskolin+Go6983+
TTNPB+EPZ004777+5-Aza-2'-deoxycytidine+Parnate;
VPA+CHIR99021+Repsox+Forskolin+Go6983+
TTNPB+EPZ004777+AM580+5-Aza-2'-deoxycytidine+
Parnate;
VPA+CHIR99021+Repsox+Forskolin+Go6983+
TTNPB+EPZ004777+5-Aza-2'-deoxycytidine+SP600125+
Parnate;
VPA+CHIR99021+Repsox+Forskolin+Go6983+
TTNPB+EPZ004777+5-Aza-2'-deoxycytidine+SP600125+
AM580+Parnate;
VPA+CHIR99021+Repsox+Forskolin+Go6983+
TTNPB+EPZ004777+SP600125+Parnate;
VPA+CHIR99021+Repsox+Forskolin+Go6983+
TTNPB+EPZ004777+AM580+SP600125+Parnate;
VPA+CHIR99021+Repsox+Forskolin+Go6983+
TTNPB+EPZ004777+AM580+SP600125+Y27632+Parnate;
VPA+CHIR99021+Repsox+Forskolin+Go6983+
TTNPB+EPZ004777+AM580+SP600125+Y27632+5-Aza-
2'-deoxycytidine+Parnate;
VPA+CHIR99021+Repsox+Forskolin+Go6983+
TTNPB+EPZ004777+AM580+SP600125+Y27632+5-Aza-
2'-deoxycytidine+ascorbate+Parnate;
VPA+CHIR99021+Repsox+Forskolin+Go6983+
TTNPB+EPZ004777+AM580+SP600125+Y27632+ascorbate+Parnate;
VPA+CHIR99021+Repsox+Forskolin+Go6983+
TTNPB+EPZ004777+AM580+Y27632+ascorbate+Parnate;
VPA+CHIR99021+Repsox+Forskolin+Go6983+
TTNPB+EPZ004777+AM580+Y27632+ascorbate+5-Aza-
2'-deoxycytidine+Parnate.

As a further optimization, the first stage contact activation component is any of the following:
CHIR99021+Repsox;
BIO+Repsox;
BIO+SB431542;
CHIR99021+SB431542;
BIO+SB431542;
VPA+SB431542;
VPA+Repsox;
VPA+CHIR99021+Repsox;
VPA+CHIR99021+SB431542;
VPA+BIO+Repsox;
VPA+BIO+SB431542;
CHIR99021+Repsox+Forskolin;
CHIR99021+Repsox+Rolipram;
BIO+Repsox+Rolipram;
BIO+SB431542+Rolipram;
BIO+SB431542+Forskolin;
BIO+Repsox+Forskolin;
CHIR99021+SB431542+Rolipram;
CHIR99021+SB431542+Forskolin;
VPA+CHIR99021+Repsox+Forskolin;
VPA+BIO+Repsox+Forskolin;
VPA+CHIR99021+Repsox+Rolipram;
VPA+CHIR99021+SB431542+Forskolin;
VPA+SB431542+Rolipram;
WA+Repsox+Rolipram;
VPA+SB431542+Forskolin;
VPA+Repsox+Forskolin;
CHIR99021+Repsox+Forskolin+Parnate;
VPA+CHIR99021+Repsox+Forskolin+Parnate;
VPA+CHIR99021+Repsox+Parnate;
CHIR99021+Repsox+Parnate;
BIO+Repsox+Parnate;
BIO+SB431542+Parnate;
CHIR99021+SB431542+Parnate;
VPA+SB431542+Parnate;
VPA+Repsox+Parnate;
VPA+Repsox+Forskolin+Parnate;
CHIR99021+Repsox+Parnate;
VPA+Repsox+Parnate;
VPA+CHIR99021+Repsox+Forskolin+Parnate;

The second stage contact induction component is any of the following:
VPA+CHIR99021+Repsox+Forskolin+Go6983;
VPA+CHIR99021+SB431542+Forskolin+Go6983;
BIO+SB431542+Forskolin+Go6983;
CHIR99021+Repsox+Forskolin+Go6983+Rolipram;
CHIR99021+Repsox+Forskolin+Go6983+Rolipram+
SB431542;
CHIR99021+SB431542+Forskolin+Go6983+Rolipram;
BIO+SB431542+Forskolin+Go6983+Rolipram;
VPA+CHIR99021+Repsox+Forskolin+Go6983+NaB;
CHIR99021+Repsox+Forskolin+Go6983+NaB;
VPA+BIO+SB431542+Rolipram+Go6983;
BIO+SB431542+Rolipram+SP600125+Go6983;
VPA+BIO+SB431542+Forskolin+Go6983;
VPA+CHIR99021+SB431542+Rolipram+Go6983;
VPA+CHIR99021+Repsox+Forskolin+Go6983+
SP600125;
VPA+CHIR99021+Repsox+Forskolin+Go6983+8-
pCPT-2'-O-Me-cAMP;
VPA+CHIR99021+Repsox+Forskolin+Go6983+
SB431542;
VPA+CHIR99021+SB431542+Forskolin+Go6983+Tranilast;
VPA+CHIR99021+Repsox+Forskolin+Go6983+
SB431542+A8301;
VPA+CHIR99021+Repsox+Forskolin+Go6983+Rolipram+SB431542+A8301;
VPA+CHIR99021+Repsox+Forskolin+Go6983+Rolipram+SB431542;
VPA+CHIR99021+Repsox+Forskolin+Go6983+
SP600125+Parnate;
VPA+CHIR99021+Repsox+Forskolin+Go6983+Rolipram;
VPA+CHIR99021+Repsox+Forskolin+Go6983+Rolipram+SB431542;
VPA+CHIR99021+Repsox+Rolipram+Go6983;
VPA+CHIR99021+Repsox+Forskolin+Go6983+Parnate;
VPA+BIO+Repsox+Forskolin+Go6983;
CHIR99021+Repsox+Forskolin+Go6983;
CHIR99021+Repsox+Rolipram+Go6983;
CHIR99021+SB431542+Forskolin+Go6983;
CHIR99021+SB431542+Rolipram+Go6983;
CHIR99021+Repsox+Forskolin+SP600125+Go6983;

CHIR99021+Repsox+Forskolin+SP600125+Parnate+Go6983;
BIO+Repsox+Forskolin+Go6983+Rolipram;
BIO+Repsox+Forskolin+Go6983;
BIO+Repsox+Forskolin+Go6983+SP600125;
BIO+SB431542+Rolipram+Go6983;
BIO+SB431542+Rolipram+Go6983+SP600125;
BIO+SB431542+Rolipram+Go6983+SP600125+Parnate;
VPA+BIO+SB431542+Rolipram+Go6983+SP600125;
VPA+CHIR99021+Repsox+Forskolin+Go6983+5-Aza-2'-deoxycytidine;
VPA+CHIR99021+Repsox+Forskolin+Go6983+SP600125+5-Aza-2'-deoxycytidine;
VPA+CHIR99021+Repsox+Forskolin+Go6983+TTNPB+EPZ004777;
VPA+CHIR99021+Repsox+Forskolin+Go6983+TTNPB+EPZ004777+AM580;
VPA+CHIR99021+Repsox+Forskolin+Go6983+TTNPB+EPZ004777+5-Aza-2'-deoxycytidine;
VPA+CHIR99021+Repsox+Forskolin+Go6983+TTNPB+EPZ004777+AM580+5-Aza-2'-deoxycytidine;
VPA+CHIR99021+Repsox+Forskolin+Go6983+TTNPB+EPZ004777+5-Aza-2'-deoxycytidine+SP600125;
VPA+CHIR99021+Repsox+Forskolin+Go6983+TTNPB+EPZ004777+5-Aza-2'-deoxycytidine+SP600125+AM580;
VPA+CHIR99021+Repsox+Forskolin+Go6983+TTNPB+EPZ004777+SP600125;
VPA+CHIR99021+Repsox+Forskolin+Go6983+TTNPB+EPZ004777+AM580+SP600125;
VPA+CHIR99021+Repsox+Forskolin+Go6983+TTNPB+EPZ004777+AM580+SP600125+Y27632;
VPA+CHIR99021+Repsox+Forskolin+Go6983+TTNPB+EPZ004777+AM580+SP600125+Y27632+5-Aza-2'-deoxycytidine;
VPA+CHIR99021+Repsox+Forskolin+Go6983+TTNPB+EPZ004777+AM580+SP600125+Y27632+5-Aza-2'-deoxycytidine+ascorbate;
VPA+CHIR99021+Repsox+Forskolin+Go6983+TTNPB+EPZ004777+AM580+SP600125+Y27632+ascorbate;
VPA+CHIR99021+Repsox+Forskolin+Go6983+TTNPB+EPZ004777+AM580+Y27632+ascorbate;
VPA+CHIR99021+Repsox+Forskolin+Go6983+TTNPB+EPZ004777+AM580+Y27632+ascorbate+5-Aza-2'-deoxycytidine;
VPA+CHIR99021+Repsox+Forskolin+Go6983+TTNPB+EPZ004777+Parnate;
VPA+CHIR99021+Repsox+Forskolin+Go6983+TTNPB+EPZ004777+AM580+Parnate;
VPA+CHIR99021+Repsox+Forskolin+Go6983+TTNPB+EPZ004777+5-Aza-2'-deoxycytidine+Parnate;
VPA+CHIR99021+Repsox+Forskolin+Go6983+TTNPB+EPZ004777+AM580+5-Aza-2'-deoxycytidine+Parnate;
VPA+CHIR99021+Repsox+Forskolin+Go6983+TTNPB+EPZ004777+5-Aza-2'-deoxycytidine+SP600125+Parnate;
VPA+CHIR99021+Repsox+Forskolin+Go6983+TTNPB+EPZ004777+5-Aza-2'-deoxycytidine+SP600125+AM580+Parnate;
VPA+CHIR99021+Repsox+Forskolin+Go6983+TTNPB+EPZ004777+SP600125+Parnate;
VPA+CHIR99021+Repsox+Forskolin+Go6983+TTNPB+EPZ004777+AM580+SP600125+Parnate;
VPA+CHIR99021+Repsox+Forskolin+Go6983+TTNPB+EPZ004777+AM580+SP600125+Y27632+Parnate;
VPA+CHIR99021+Repsox+Forskolin+Go6983+TTNPB+EPZ004777+AM580+SP600125+Y27632+5-Aza-2'-deoxycytidine+Parnate;
VPA+CHIR99021+Repsox+Forskolin+Go6983+TTNPB+EPZ004777+AM580+SP600125+Y27632+5-Aza-2'-deoxycytidine+ascorbate+Parnate;
VPA+CHIR99021+Repsox+Forskolin+Go6983+TTNPB+EPZ004777+AM580+SP600125+Y27632+ascorbate+Parnate;
VPA+CHIR99021+Repsox+Forskolin+Go6983+TTNPB+EPZ004777+AM580+Y27632+ascorbate+Parnate;
VPA+CHIR99021+Repsox+Forskolin+Go6983+TTNPB+EPZ004777+AM580+Y27632+ascorbate+5-Aza-2'-deoxycytidine+Parnate.

The effective concentration of specific small molecule compounds in enumerated implementation solutions is as follows. The concentration range given below is only for reference, and could be adaptively modified on this basis. If other small molecules replace the following ones, the concentration could also be adaptively adjusted.

Forskolin concentration ranges from 2 µM to 20 µM; Repsox concentration ranges from 2 µM to 15 µM; CHIR99021 concentration ranges from 1 µM to 10 µM; VPA concentration ranges from 0.5 mM to 1.5 mM; TTNPB concentration ranges from 3 µM to 8 µM; AM580 concentration ranges from 0.03 µM to 0.08 µM; EPZ004777 concentration ranges from 3 µM to 8 µM; Go6983 concentration ranges from 1 µM to 15 µM; Y-27632 concentration ranges from 3 µM to 15 µM; L-Ascorbinacid 2-phosphate concentration ranges from 0.15 mM to 0.25 mM; SP600125 concentration ranges from 1 µM to 15 µM; and 5-Aza-2'-deoxycytidine ranges from 0.5 µM to 15 µM.

The induced mesenchymal stem cells obtained by the present invention have the molecular characteristics of natural mesenchymal stem cells. The induced mesenchymal stem cells can be expanded trillions of times with large quantities and high purity, having good industrial prospects. Cells of different lineages could also be obtained by inducing differentiated cells using the method of the present invention or through adaptive adjustment based on the method of the present invention. If the combinations of small molecule compounds in the present invention are used to prepare different cells in addition to MSCs, the concentration and/or the combination of small molecule compounds could be adjusted according to actual needs.

Small molecules suitable for different signaling pathways have been widely reported in the art, and those skilled in the art are continually developing such molecules. In the present invention, there are no particular limitations on the structure or classification of the small molecule compounds, while the molecules are required to be capable of performing the functions of inhibiting or activating lysine deacetylases, TGF-β, PKC, DNMT, HMT, JNK, ROCK, WNT/β-catenin, cAMP, RA (Retinoic acid) signaling pathways. Therefore, the present invention covers all molecules capable of performing the functions of inhibiting or activating lysine deacetylases, TGF-β, PKC, DNMT, HMT, histone demethylases, JNK, ROCK, WNT/β-catenin, cAMP, RA (Retinoic acid), and covers any alternatives for achieving the inhibition or activation of the above targets.

Compared with the prior art, the present invention has the following advantages: the differentiated cell is induced into MSC by regulating corresponding signaling pathways and/ or enzyme activities in stages timely, which is easy to be precisely controlled and standardized; the biopsy specimen is small, the collection is convenient and the sources are wide; the induced mesenchymal stem cells and related products are available for high scale and personalized preparation, which could be widely used in the basic medical research, clinical treatment and tissue engineering product research and development, with industrialization prospects.

DETAILED DESCRIPTION OF THE EMBODIMENTS

Figure 1:
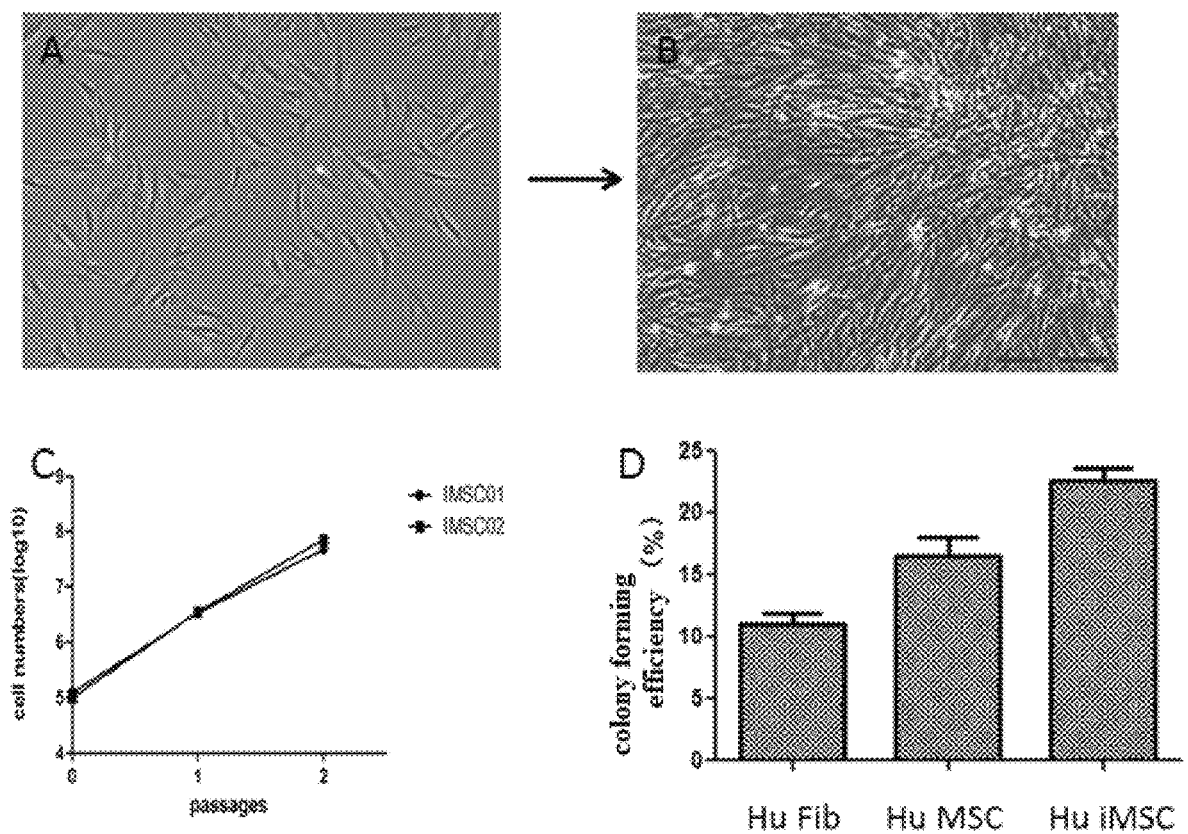
FIG. 1 is a diagram showing cell morphology of reprogramming human skin fibroblasts to induced mesenchymal stem cells by small molecule compounds.

The technical solutions of the present invention are further described in detail below with reference to the drawings and specific embodiments, while the present invention is not limited to the following experimental solutions.

Embodiment 1

1. Isolation of Skin Fibroblasts
1.1 A skin biopsy specimen of 1 cm in diameter was derived from donor, and the primary fibroblasts were isolated by tissue adherence method. The isolated fibroblasts were cultured in a basic culture medium containing 10% fetal bovine serum (Hyclone), 100 U/mL penicillin (Sigma), 100 μg/mL streptomycin (Sigma), and High-Glucose DMEM.
1.2 Cells were proliferated through passage and fibroblasts at $6^{th}$ to $12^{th}$ generations were used to transdifferentiate into mesenchymal stem cells. On the day before the initiation of differentiation (Day-1), the cells were seeded at a density of $1\times10^4$-$2.5\times10^4$/cm$^2$ in an incubator under a condition of 37° C. and 5% $CO_2$.
2. Activation of Skin Fibroblasts
2.1 At the time of initiation of transdifferentiation (Day 0), the basic medium was completely replaced with a first-stage culture medium for culturing the cells for 4-6 days. The first-stage culture medium contains 10% fetal bovine serum (Hyclone), 100 U/ml penicillin (Sigma), 100 Ng/ml streptomycin (Sigma), High-Glucose DMEM medium (Gibco), forskolin (2 μM-25 μM), Repsox (2 μM-15 μM), CHIR99021 (1 μM-10 μM), and VPA (0.5 mM-1.5 mM). In this culture system, the 10% fetal bovine serum can also be replaced by serum substitutes (invitrogen) at a concentration of 10%-20%; and 100 U/mL penicillin (Sigma) and 100 μg/mL streptomycin (Sigma) may not be used. The cells were cultured under the condition of 37° C. and 5% $CO_2$.
3. Directed Induction of Skin Fibroblasts After the treatment of the second step mentioned above was completed, the cell culture medium was completely replaced by a second-stage culture medium. The culture time was ranged from 6 days to 10 days, and the cells were cultured at 37° C. and 5% $CO_2$ condition. The second-stage culture medium contains: 10% fetal bovine serum (Hyclone), 100 U/mL penicillin (Sigma), 100 μg/mL streptomycin (Sigma), High-Glucose DMEM medium (Gibco), forskolin (2 μM-20 μM), Repsox (2 μM-15 μM), CHIR99021 (1 μM-10 μM), VPA (0.5 mM-1.5 mM), TTNPB (3 μM-8 μM), AM580 (0.03 μM-0.08 μM), EPZ004777 (3 μM-8 μM), Go6983 (1 μM-15 μM), Y-27632 (3 μM-15 μM), and L-Ascorbin acid 2-phosphate (0.15 mM-0.25 mM). In this culture system, the 10% fetal bovine serum can also be replaced by serum substitutes (invitrogen) at a concentration of 10%-20%; and 100 U/mL penicillin (Sigma) and 100 μg/mL streptomycin (Sigma) may not be used.
4. Improving the Efficiency of Transdifferentiation to Mesenchymal Stem Cells in the Third Stage Subsequently, the cells were cultured in a third-stage culture medium for 3-8 days under the condition of 37° C. and 5% $CO_2$. The third stage culture medium contains BMP4 (10-20 μg/mL), PDGF-AB (100-250 μg/mL), b-FGF (10-50 μg/mL), 10% fetal bovine serum (Hyclone), 100 U/ml penicillin (Sigma), 100 μg/mL streptomycin (Sigma), and High-Glucose DMEM medium (Gibco). In this culture system, 10% fetal bovine serum can also be replaced by 10%-20% serum substitute (invitrogen); and 100 U/mL penicillin (Sigma) and 100 μg/mL penicillin (Sigma) may not be used.
5. Maintenance Culture and Expansion of Induced Mesenchymal Stem Cells Subsequently, the medium was replaced by conventional mesenchymal stem cell culture medium or commercially available mesenchymal stem cell culture medium (Cyagen) for culture and expansion. The conventional mesenchymal stem cell culture medium contains 10% fetal bovine serum (Hyclone), 100 U/mL penicillin (Sigma), 100 μg/mL streptomycin (Sigma), and High-Glucose DMEM medium (Gibco).

Embodiment 2

1. Isolation of Skin Fibroblasts, as Described in Embodiment 1.
2. At the time of initiation of transdifferentiation (Day 0), the basic culture medium was completely replaced by the following second-stage culture medium. The cells were cultured for 4-12 days under the condition of 37° C. and 5% $CO_2$. The second-stage culture medium contains: 10% fetal bovine serum (Hyclone), 100 U/mL penicillin (Sigma), 100 μ/mL streptomycin (Sigma), High-Glucose DMEM medium (Gibco), forskolin (2 μM-20 μM), Repsox (2 μM-15 μM), CHIR99021 (1 μM-10 μM), VPA (0.5 mM-1.5 mM), TTNPB (3 μM-8 μM), AM580 (0.03 μM-0.08 μM), EPZ004777 (3 μM-8 μM), Go6983 (1 μM-15 μM), Y-27632 (3 μM-15 μM), and L-Ascorbin acid 2-phosphate (0.15 mM-0.25 mM). In this culture system, the 10% fetal bovine serum can also be replaced by serum substitutes (invitrogen) at a concentration of 10%-20%; and 100 U/mL penicillin (Sigma) and 100 μg/mL streptomycin (Sigma) may not be used.

3. Subsequently, the cells were cultured in the following stage culture medium for 3-8 days under 37° C. and 5% $CO_2$ condition. The stage culture medium contains BMP4 (10-20 μg/mL), PDGF-AB (100-250 μg/mL), b-FGF (10-50 μg/mL), 10% fetal bovine serum (Hyclone), 100 U/ml penicillin (Sigma), 100 μg/ml streptomycin (Sigma), and High Glucose DMEM medium (Gibco). In this culture system, 10% fetal bovine serum can also be replaced by serum substitute (invitrogen) at a concentration of 10%-20%; and 100 U/mL penicillin (Sigma) and 100 μg/mL streptomycin (Sigma) may not be used.

4. Maintenance Culture and Expansion of Induced Mesenchymal Stem Cells

Subsequently, the medium was replaced with conventional mesenchymal stem cell culture medium or commercially available mesenchymal stem cell culture medium (Cyagen) for culture and expansion. The conventional mesenchymal stem cell culture medium contains: 10% fetal bovine serum (Hyclone), 100 U/mL penicillin (Sigma), 100 μg/mL streptomycin (Sigma), and High-Glucose DMeM medium (Gibco).

Embodiment 3

1. Isolation of Skin Fibroblasts, as Described in Embodiment 1.

2. Activation of Skin Fibroblasts 2.1 At the time of initiation of transdifferentiation (Day 0), the basic culture medium was completely replaced by the first-stage culture medium for culturing the cells for 4-6 days. The first-stage culture medium contains 10% fetal bovine serum (Hyclone), 100 U/mL penicillin (Sigma), 100 μg/mL streptomycin (Sigma), High-Glucose DMeM medium (Gibco), forskolin (2 μM-25 μM), Repsox (2 μM-15 μM), CHIR99021 (1 μM-10 μM), and VPA (0.5 mM-1.5 mM). In this culture system, the 10% fetal bovine serum can also be replaced by serum substitutes (invitrogen) at a concentration of 10%-20%; and 100 U/mL penicillin (Sigma) and 100 μg/mL streptomycin (Sigma) may not be used. The cells were cultured under 37° C. and 5% $CO_2$ condition.

3. Directed Induction of Skin Fibroblasts

After the treatment of the second step mentioned above was completed, the cell culture medium was completely replaced by the second-stage culture medium. The culture time was ranging from 6 days to 10 days, and the cells were cultured under 37° C. and 5% $CO_2$ condition. The second-stage culture medium described contains: 10% fetal bovine serum (Hyclone), 100 U/mL penicillin (Sigma), 100 μg/mL streptomycin (Sigma), High-Glucose DMEM medium (Gibco), forskolin (2 μM-20 μM), Repsox (2 μM-15 μM), CHIR99021 (1 μM-10 μM), VPA (0.5 mM-1.5 mM), TTNPB (3 μM-8 μM), AM580 (0.03 μM-0.08 μM), EPZ004777 (3 μM-8 μM), Go6983 (1 μM-15 μM), Y-27632 (3 μM-15 μM), and L-Ascorbin acid 2-phosphate (0.15 mM-0.25 mM). In this culture system, the 10% fetal bovine serum can also be replaced by serum substitutes (invitrogen) at a concentration of 10%-20%; and 100 U/mL penicillin (Sigma) and 100 μg/mL streptomycin (Sigma) may not be used.

4. Maintenance Culture and Expansion of Induced Mesenchymal Stem Cells

Subsequently, the medium was replaced by conventional mesenchymal stem cell culture medium or commercially available mesenchymal stem cell culture medium (Cyagen) for culture and expansion. The conventional mesenchymal stem cell culture medium contains: 10% fetal bovine serum (Hyclone), 100 U/mL penicillin (Sigma), 100 μg/mL streptomycin (Sigma), and High-Glucose DMEM medium (Gibco).

Embodiment 4

1. Isolation of Skin Fibroblasts, as Described in Embodiment 1.

2. Activation of Skin Fibroblasts 2.1 At the time of initiation of transdifferentiation (Day 0), the basic culture medium was completely replaced by the first-stage culture medium for 4-6 days. The first stage culture medium contains 10% fetal bovine serum (Hyclone), 100 U/mL penicillin (Sigma), 100 μg/mL streptomycin (Sigma), High-Glucose DMEM medium (Gibco), forskolin (2 μM-25 μM), Repsox (2 μM-15 μM), and CHIR99021 (1 μM-10 μM). In this culture system, the 10% fetal bovine serum can also be replaced by serum substitutes (invitrogen) at a concentration of 10%-20%; and 100 U/mL penicillin (Sigma) and 100 μg/mL streptomycin (Sigma) may not be used. The cells were cultured under 37° C. and 5% $CO_2$ condition.

3. Directed Induction of Skin Fibroblasts

After the treatment of the second step mentioned above was completed, the cell culture medium was completely replaced by the second-stage culture medium. The culture time was ranging from 6 days to 10 days, and the cells were cultured under 37° C. and 5% $CO_2$ condition. The second-stage culture medium contains: 10% fetal bovine serum (Hyclone), 100 U/mL penicillin (Sigma), 100 μg/mL streptomycin (Sigma), High-Glucose DMEM medium (Gibco), forskolin (2 μM-20 μM), Repsox (2 μM-15 μM), CHIR99021 (1 μM-10 μM), VPA (0.5 mM-1.5 mM), TTNPB (3 μM-8 μM), AM580 (0.03 μM-0.08 μM), EPZ004777 (3 μM-8 μM), Go6983 (1 μM-15 μM), Y-27632 (3 μM-15 μM), L-Ascorbin acid 2-phosphate (0.15 mM-0.25 mM), and SP600125 (1 μM-15 μM). In this culture system, 10% fetal bovine serum can also be replaced by serum substitutes (invitrogen) at a concentration of 10%-20%; and 100 U/mL penicillin (Sigma) and 100 μg/mL streptomycin (Sigma) may not be used.

4. Improving the Efficiency of Transdifferentiation to Mesenchymal Stem Cell in the Third Stage Subsequently, the cells were cultured in the third-stage medium for 3-8 days under the condition of 37° C. and 5% $CO_2$. The third stage culture medium contains BMP4 (10-20 μg/mL), PDGF-AB (100-250 μg/mL), b-FGF (10-50 μg/mL), 10% fetal bovine serum (Hyclone), 100 U/mL penicillin (Sigma), 100 μg/mL streptomycin (Sigma), and High-Glucose DMEM medium (Gibco). In this culture system, 10% fetal bovine serum can also be replaced by serum substitutes (invitrogen) at a concentration of 10%-20%; and 100 U/mL penicillin (Sigma) and 100 μg/mL streptomycin (Sigma) may not be used.

5. Maintenance Culture and Expansion of Induced Mesenchymal Stem Cells

Subsequently, the medium was replaced with conventional mesenchymal stem cell culture medium or commercially available mesenchymal stem cell culture medium (Cyagen) for maintenance and expansion. The conventional mesenchymal stem cell culture medium contains: 10% fetal bovine serum (Hyclone), 100 U/mL penicillin (Sigma), 100 μg/mL streptomycin (Sigma), and High-Glucose DMEM medium (Gibco).

Embodiment 5

1. Isolation of Skin Fibroblasts, as Described in Embodiment 1.

2. Activation of Skin Fibroblasts 2.1 At the time of initiation of transdifferentiation (Day 0), the basic medium was completely replaced by the first stage culture medium for 4-6 days. The first stage culture medium contains 10% fetal bovine serum (Hyclone), 100 U/mL penicillin (Sigma), 100 μg/mL streptomycin (Sigma), High-Glucose DMEM medium (Gibco), forskolin (2 μM-25 μM), Repsox (2 μM-15 μM), CHIR99021 (1 μM-10 μM), and VPA (0.5 mM-1.5 mM). In this culture system, 10% fetal bovine serum can also be replaced by serum substitutes (invitrogen) at a concentration of 10%-20%; and 100 U/mL penicillin (Sigma) and 100 μg/mL streptomycin (Sigma) may not be used. The cells were cultured under 37° C. and 5% $CO_2$ condition.

3. Directed Induction of Skin Fibroblasts

After the treatment of the second step mentioned above was completed, the cell culture medium was completely replaced by the second-stage culture medium. The culture time was ranging from 6 days to 10 days, and the cells were cultured under 37° C. and 5% $CO_2$ condition. The second-stage culture medium contains: 10% fetal bovine serum (Hyclone), 100 U/mL penicillin (Sigma), 100 μg/mL streptomycin (Sigma), High-Glucose DMEM medium (Gibco), forskolin (2 μM-20 μM), Repsox (2 μM-15 μM), CHIR99021 (1 μM-10 μM), VPA (0.5 mM-1.5 mM), TTNPB (3 μM-8 μM), AM580 (0.03 μM-0.08 μM), EPZ004777 (3 μM-8 μM), Go6983 (1 μM-15 μM), Y-27632 (3 μM-15 μM), L-Ascorbin acid 2-phosphate (0.15 mM-0.25 mM), SP600125 (8 μM-12 μM), and 5-Aza-2'-deoxycytidine (1 μM-15 μM). In this culture system, 10% fetal bovine serum can also be replaced by serum substitutes (invitrogen) at concentrations of 10%-20%; and 100 U/mL penicillin (Sigma) and 100 μg/mL streptomycin (Sigma) also may not be used.

4. Improving the Efficiency of Transdifferentiation to Mesenchymal Stem Cell in the Third Stage Subsequently, the cells were cultured in the third-stage medium for 3 to 8 days under the condition of 37° C. and 5% $CO_2$. The third-stage culture medium contains BMP4 (10-20 μg/mL), PDGF-AB (100-250 μg/mL), b-FGF (10-50 μg/mL), 10% fetal bovine serum (Hyclone), 100 U/mL penicillin (Sigma), 100 μg/mL streptomycin (Sigma), and High Glucose DMEM medium (Gibco). In this culture system, 10% fetal bovine serum can also be replaced by serum substitutes (invitrogen) at a concentration of 10%-20%; and 100 U/mL penicillin (Sigma) and 100 μg/mL streptomycin (Sigma) also may not be used.

5. Maintenance Culture and Expansion of Induced Mesenchymal Stem Cells

Subsequently, the medium was replaced by conventional mesenchymal stem cell culture medium or commercially available mesenchymal stem cell culture medium (Cyagen) for maintenance and expansion. The conventional mesenchymal stem cell culture medium contains: 10% fetal bovine serum (Hyclone), 100 U/mL penicillin (Sigma), 100 μg/mL streptomycin (Sigma), and High-Glucose DMEM medium (Gibco).

Embodiment 6

1. Isolation of Skin Fibroblasts, as Described in Embodiment 1.

2. Activation of Skin Fibroblasts 2.1 At the time of initiation of transdifferentiation (Day 0), the basic medium was completely replaced by the first-stage culture medium for 4-6 days. The first-stage culture medium contains 10% fetal bovine serum (Hyclone), 100 U/mL penicillin (Sigma), 100 μg/mL streptomycin (Sigma), High-Glucose DMEM medium (Gibco), forskolin (2 μM-25 μM), Repsox (2 μM-15 μM), CHIR99021 (1 μM-10 μM), and VPA (0.5 mM-1.5 mM). In this culture system, 10% fetal bovine serum can also be replaced by serum substitutes (invitrogen) at concentrations of 10%-20%; and 100 U/mL penicillin (Sigma) and 100 μg/mL streptomycin (Sigma) may not be used. The cells were cultured under 37° C. and 5% $CO_2$ condition.

3. Directed Induction of Skin Fibroblasts

After the treatment of the second step mentioned above was completed, the cell culture medium was completely replaced by the second-stage culture medium. The culture time was ranging from 6 days to 10 days, and the cells were cultured under 37° C. and 5% $CO_2$ condition. The second-stage culture medium contains: 10% fetal bovine serum (Hyclone), 100 U/mL penicillin (Sigma), 100 μg/mL streptomycin (Sigma), High-Glucose DMEM medium (Gibco), forskolin (2 μM-20 μM), Repsox (2 μM-15 μM), CHIR99021 (1 μM-10 μM), VPA (0.5 mM-1.5 mM), TTNPB (3 μM-8 μM), AM580 (0.03 μM-0.08 μM), EPZ004777 (3 μM-8 μM), Go6983 (1 μM-15 μM), Y-27632 (3 μM-15 μM), L-Ascorbin acid 2-phosphate (0.15 mM-0.25 mM), SP600125 (8 μM-12 μM), 5-Aza-2'-deoxycytidine (1 μM-15 μM), Parnate (1 μM-10 μM). In this culture system, 10% fetal bovine serum can also be replaced by serum substitutes (invitrogen) at concentrations of 10%-20%; and 100 U/mL penicillin (Sigma) and 100 μg/mL streptomycin (Sigma) also may not be used.

4. Improving the Efficiency of Transdifferentiation to Mesenchymal Stem Cell in the Third Stage Subsequently, the cells were cultured in the third-stage medium for 3-8 days under the condition of 37° C. and 5% $CO_2$. The third stage culture medium contains BMP4 (10-20 μg/mL), PDGF-AB (100-250 μg/mL), b-FGF (10-50 μg/mL), 10% fetal bovine serum (Hyclone), 100 U/mL penicillin (Sigma), 100 μg/mL streptomycin (Sigma), and High-Glucose DMEM medium (Gibco). In this culture system, 10% fetal bovine serum can also be replaced by serum substitutes (invitrogen) at concentrations of 10%-20%; and 100 U/ml penicillin (Sigma) and 100 μg/ml streptomycin (Sigma) may not be used.

5. Maintenance Culture and Expansion of Induced Mesenchymal Stem Cells

Subsequently, the medium was replaced with conventional mesenchymal stem cell culture medium or commercially available mesenchymal stem cell culture medium (Cyagen) for maintenance and expansion. The conventional mesenchymal stem cell culture medium contains: 10% fetal bovine serum (Hyclone), 100 U/mL penicillin (Sigma), 100 μg/mL streptomycin (Sigma), and High-Glucose DMEM medium (Gibco).

Embodiment 7

1. Isolation of Skin Fibroblasts, as Described in Embodiment 1.
2. Activation of Skin Fibroblasts 2.1 At the time of initiation of transdifferentiation (Day 0), the basic medium was completely replaced by the first-stage culture medium for 4-6 days. The first-stage culture medium contains 10% fetal bovine serum (Hyclone), 100 U/mL penicillin (Sigma), 100 μg/mL streptomycin (Sigma), High-Glucose DMEM medium (Gibco), forskolin (2 μM-25 μM), Repsox (2 μM-15 μM), BIO (1 μM-10 μM), and VPA (0.5 mM-1.5 mM). In this culture system, 10% fetal bovine serum can also be replaced by serum substitutes (invitrogen) at concentrations of 10%-20%; and 100 U/mL penicillin (Sigma) and 100 μg/mL streptomycin (Sigma) may not be used. The cells were cultured under 37° C. and 5% $CO_2$ condition.

3. Directed Induction of Skin Fibroblasts

After the treatment of the second step mentioned above was completed, the cell culture medium was completely replaced by the second-stage culture medium. The culture time was ranging from 6 days to 10 days, and the cells were cultured under 37° C. and 5% $CO_2$ condition. The second-stage culture medium contains: 10% fetal bovine serum (Hyclone), 100 U/mL penicillin (Sigma), 100 μg/mL streptomycin (Sigma), High-Glucose DMEM medium (Gibco), forskolin (2 μM-20 μM), Repsox (2 μM-15 μM), CHIR99021 (1 μM-10 μM), VPA (0.5 mM-1.5 mM), TTNPB (3 μM-8 μM), AM580 (0.03 μM-0.08 μM), EPZ004777 (3 μM-8 μM), Go6983 (1 μM-15 μM), Y-27632 (3 μM-15 μM), L-Ascorbin acid 2-phosphate (0.15 mM-0.25 mM), SP600125 (8 μM-12 μM), 5-Aza-2'-deoxycytidine (1 μM-15 μM), and Parnate (1 μM-10 μM). In this culture system, 10% fetal bovine serum can also be replaced by serum substitutes (invitrogen) at concentrations of 10%-20%; and 100 U/ml penicillin (Sigma) and 100 μg/ml streptomycin (Sigma) may not be used.

4. Stage 3: Improving the Efficiency of Transdifferentiation to Mesenchymal Stem Cell Subsequently, the cells were cultured in the third-stage medium for 3-8 days at 37° C. and 5% $CO_2$. The third-stage culture medium contains BMP4 (10-20 μg/mL), PDGF-AB (100-250 μg/mL), b-FGF (10-50 μg/mL), 10% fetal bovine serum (Hyclone), 100 U/mL penicillin (Sigma), 100 μg/mL streptomycin (Sigma), and High-Glucose DMEM medium (Gibco). In this culture system, 10% fetal bovine serum can also be replaced by serum substitutes (invitrogen) at concentrations of 10%-20%; and 100 U/ml penicillin (Sigma) and 100 μg/ml streptomycin (Sigma) may not be used.

5. Maintenance Culture and Expansion of Induced Mesenchymal Stem Cells

Subsequently, the medium was replaced by conventional mesenchymal stem cell culture medium or commercially available mesenchymal stem cell culture medium (Cyagen) for maintenance and expansion. The conventional mesenchymal stem cell culture medium contains: 10% fetal bovine serum (Hyclone), 100 U/mL penicillin (Sigma), 100 μg/mL streptomycin (Sigma), and High-Glucose DMEM medium (Gibco).

In the above Embodiments, the human skin fibroblasts are being induced to prepare (are being reprogrammed as) mesenchymal stem cells. The cell morphology of human skin fibroblasts and their induced mesenchymal stem cells (iMSC) is shown in FIG. 1. The detection results of the induced mesenchymal stem cells are shown in Table 1, and FIGS. 2 to 7.

As shown in FIG. 1, Part A is the morphology of skin fibroblasts; Part B is the morphology of skin fibroblast-induced mesenchymal stem cells obtained by the method in Embodiment 1; Part C is the growth curve of induced mesenchymal stem cells. The iMSCs were derived from two adult individuals, respectively. The cells were cultured in a culture dish and passaged when the confluence was about 90% or passaged every three days. The induced cells had rapid proliferation. Part D is the cell clone formation rate. The higher the clone formation rate, the better the cell viability. Hu Fib represented untreated skin fibroblasts, Hu MSC represented isolated mesenchymal stem cells in vivo, Hu iMSC represented induced mesenchymal stem cells.

TABLE 1

| Antibody | HuFib 01 | HuFib 02 | HuFib 03 | Hu iMSC01 | Hu iMSC02 |
|---|---|---|---|---|---|
| CD29 | + | + | + | + | + |
| CD73 | + | + | + | + | + |
| CD105 | + | + | + | + | + |
| CD90 | + | + | + | + | + |
| CD14 | − | − | − | − | − |
| CD45 | − | − | − | − | − |
| CD34 | − | − | − | − | − |

Table 1 is the flow cytometric analysis of three untreated skin fibroblasts from different adult individuals, namely HuFib01, HuFib02 and HuFib03, and induced mesenchymal stem cells namely Hu iMSC01 and Hu iMSC02. The iMSCs meet the criteria for natural MSC identification which is positive for surface markers of CD29, CD90, CD73 and CD105, and is negative for surface markers of CD24, CD45 and CD34. Untreated skin fibroblasts have the similar characteristics for these markers.

Figure 2:
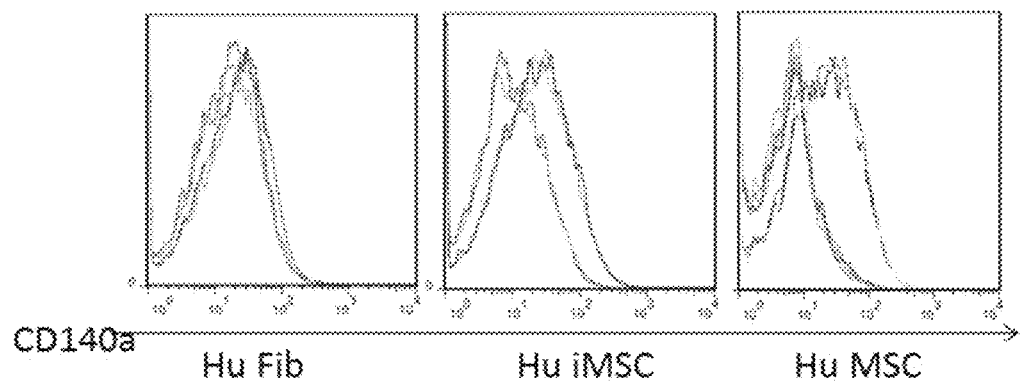
FIG. 2 is a diagram showing flow cytometric analysis of standard surface marker of natural mesenchymal stem cells to identify induced mesenchymal stem cells.

FIG. 2 is a diagram showing testing results of using another surface marker CD140a to identify mesenchymal stem cells. Compared with untreated fibroblasts Hu Fib, the peaks of Hu iMSC and Hu MSC showed a shift for the protein expression by flow cytometric analysis.

Figure 3:
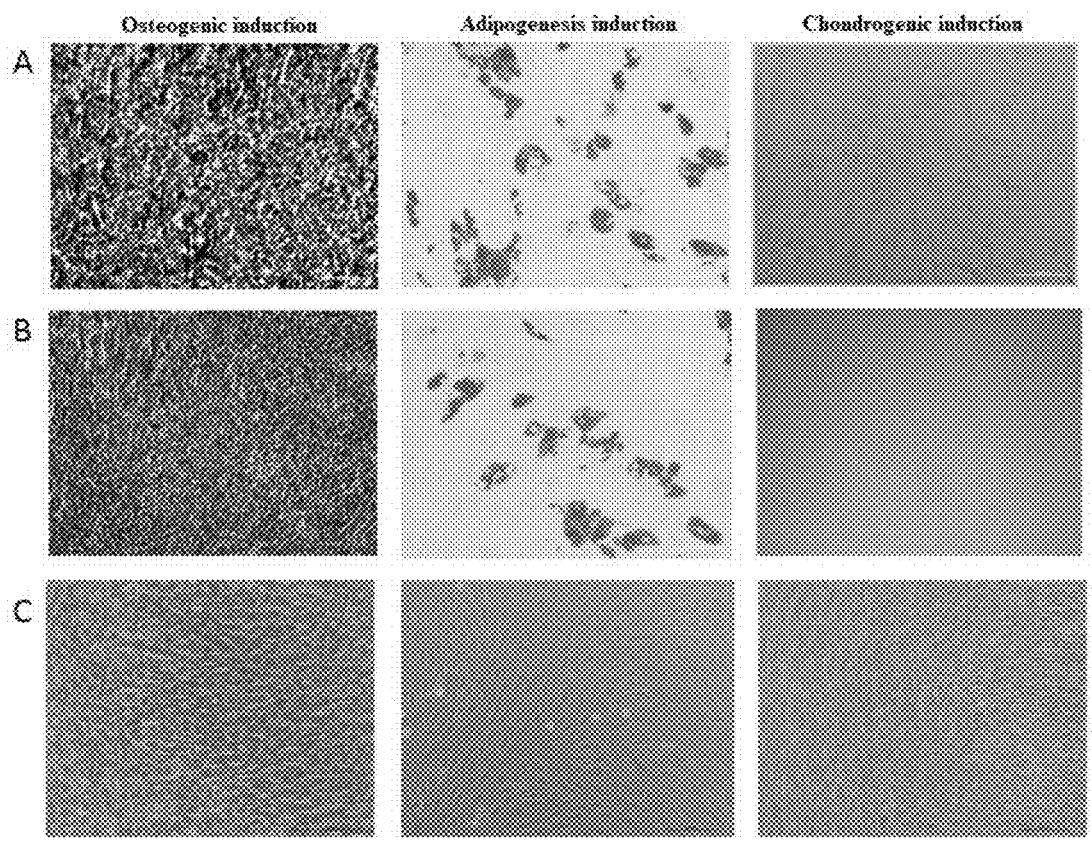
FIG. 3 is a diagram showing testing results of tri-lineage differentiation of induced mesenchymal stem cells.

FIG. 3 is a diagram showing testing results of multipotency of induced mesenchymal stem cells. As shown in FIG. 3, tri-lineage differentiation of Hu iMSC from Embodiment 1 (Part A) and Embodiment 6 (Part B) and Hu Fib (Part C) as a negative control. The generation of osteoblasts, chondrocytes, and adipocytes on day 21 was detected. Alizarin red staining was used for osteogenesis and Alcian blue used for chondrocytes differentiation and oil red O staining used for adipocytes differentiation.

Figure 4:
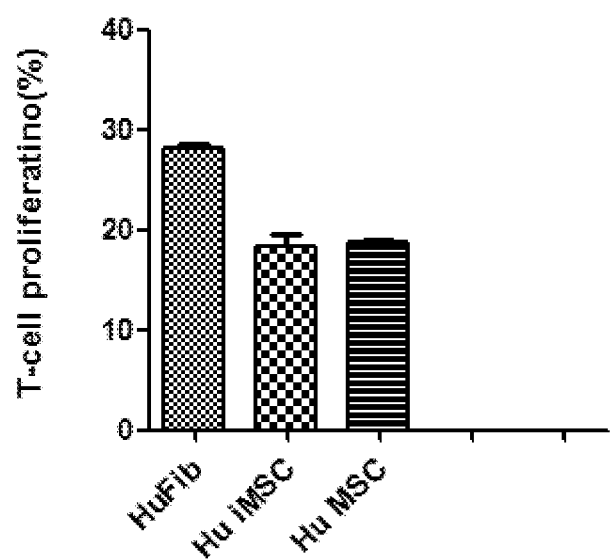
FIG. 4 is a diagram showing immunosuppressive effects of induced mesenchymal stem cells on T cells.

FIG. 4 is a diagram showing the immunosuppressive effects of induced mesenchymal stem cells on T cells. Compared with Hu Fib, the Hu iMSC and Hu MSC had similar immunosuppressive ability.

Figure 5:
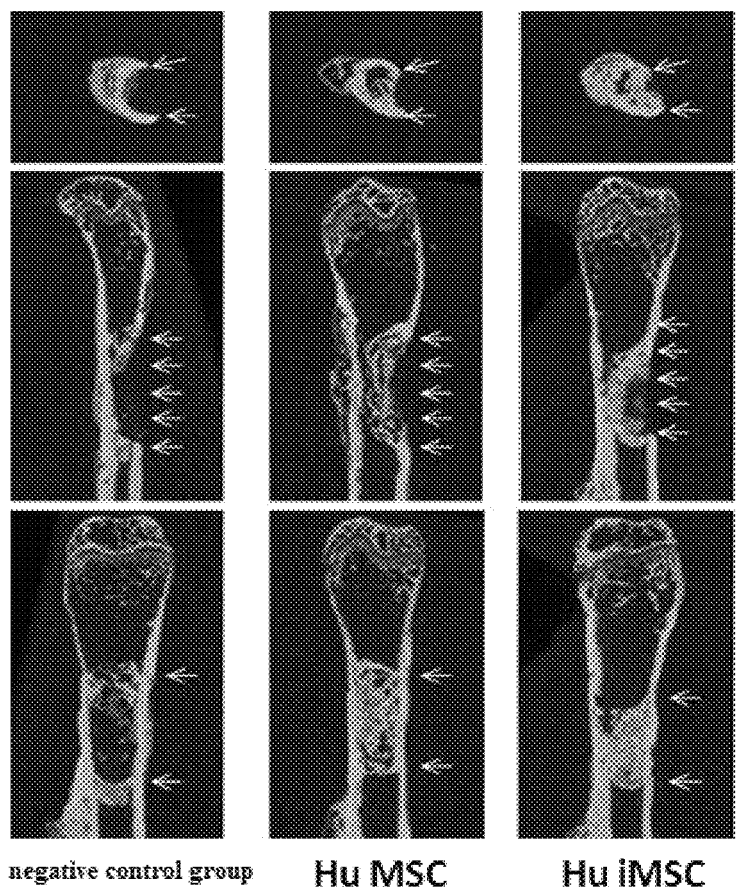
FIG. 5 is a diagram showing treatment results of transplantation of induced mesenchymal stem cells into immunodeficient mice to treat femoral defects.

FIG. 5 is a diagram showing treatment results of the transplantation of induced mesenchymal stem cells into immunodeficient mice to treat femoral defects. After 28 days of cell transplantation, microCT was used to detect the defect repair in the transplanted site. The negative control group showed on the left; MSC positive control group (Hu MSC) showed in the middle; and induced mesenchymal stem cell group showed on the right. Compared with the negative control group, the MSC and iMSC group had significant repair effect on femoral defect.

Figure 6:
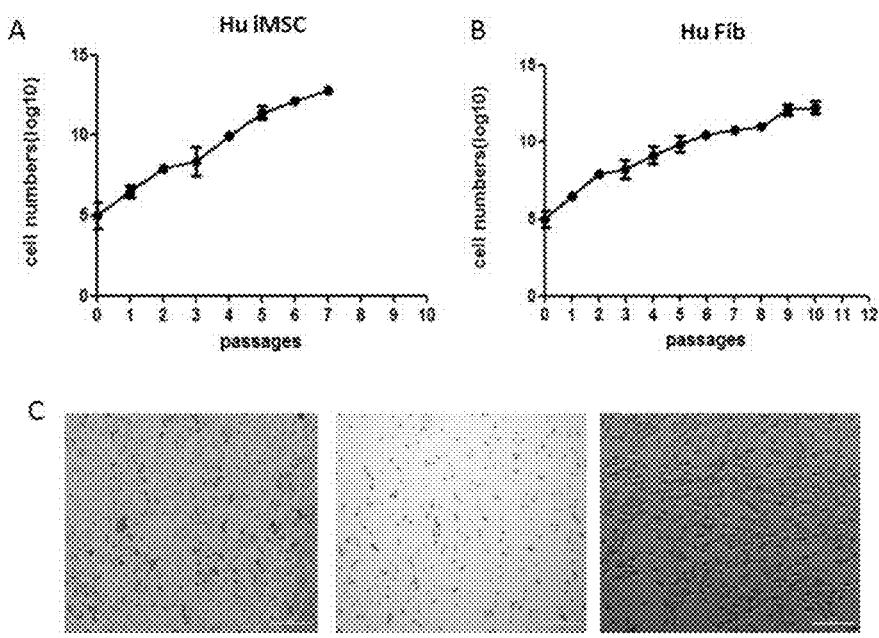
FIG. 6 is a diagram showing results of cell proliferation and tri-lineage differentiation potential for long-term passage of induced mesenchymal stem cells.

FIG. 6 is a diagram showing results of the cell proliferation and tri-lineage differentiation potential for long-term passage. As shown in FIG. 6, Part A is the growth curve of Hu iMSC from passage 0 to passage 7. Cells were passaged when the confluence was about 90% or every three days. Part B is the growth curve of skin fibroblasts from passage 0 to passage 10. Part C is the tri-lineage differentiation of Hu iMSC at passage 7 and the generation of osteoblasts, adipocytes and chondrocytes on day 21 (from left to right).

Figure 7:
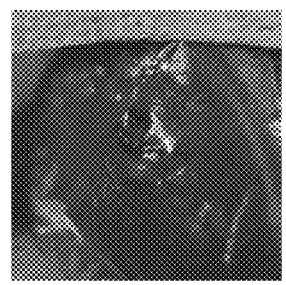
FIG. 7 is a diagram showing results of tumor formation assay of induced mesenchymal stem cells.

FIG. 7 is a diagram showing results of the tumor formation assay of induced mesenchymal stem cells. $0.6 \times 10^5$ to $1 \times 10^5$ Hu iMSCs were subcutaneously transplanted into one NOD-SCID mouse and 30 mice were transplanted. No tumor was observed after transplantation for one month.

It should be understood that, the above-mentioned characteristics of the patent technology would be combined with ones enumerated below (e.g., the Embodiments) to form a new or a preferred technical scheme. Due to limited space, more Embodiments will not be described herein.

What is claimed is:

1. A method for inducing human fibroblasts into mesenchymal stem cells, comprising: performing a directional induction on the human fibroblasts to prepare the mesenchymal stem cells, wherein the directional induction comprises treating cells by:
   inhibiting a TGF-β signal pathway with Repsox as a TGF-β signaling pathway inhibitor,
   inhibiting an activity of PKC with Go6983 as a PKC signaling pathway inhibitor,
   activating a WNT/β-catenin signal pathway with CHIR99021 as a WNT/β-catenin signaling pathway activator,
   activating a cAMP signal pathway with Forskolin as a cAMP signaling pathway activator,
   inhibiting an activity of lysine deacetylases with VPA as a lysine deacetylase inhibitor,
   activating a RA signaling pathway with TTNPB and AM580 as RA signaling pathway activators,
   inhibiting an activity of HMT with EPZ004777 as a HMT inhibitor,
   inhibiting a ROCK signaling pathway with Y-27632 as a ROCK signaling pathway inhibitor, and
   adding ascorbic acid;
   and a pretreatment step, comprising pretreating the human fibroblasts by inhibiting the activity of lysine deacetylases, inhibiting the TGF-β signal pathway, activating the WNT/β-catenin signal pathway, and activating the cAMP signal pathway.

2. The method for inducing the human fibroblasts into the mesenchymal stem cells according to claim 1, wherein the directional induction further comprises:
   inhibiting an activity of DNMT with 5-Aza-2'-deoxycytidine as a DNMT inhibitor,
   inhibiting an activity of histone demethylases with tranylcypromine as a histone demethylase inhibitor, and
   inhibiting a JNK signaling pathway with SP600125 as a JNK signaling pathway inhibitor.

3. The method for inducing the human fibroblasts into the mesenchymal stem cells according to claim 1, wherein the TGF-β signal pathway is a type I TGF-β receptors participated pathway, and the cAMP signal pathway is an EPAC/RAP1 signal pathway.

4. The method for inducing the human fibroblasts into the mesenchymal stem cells according to claim 1, wherein
   the pretreatment step comprises pretreating the human fibroblasts for about 4-6 days to obtain first treated cells; and
   the directional induction comprises:
   directionally inducing the first treated cells for about 6-10 days.

5. The method for inducing the human fibroblasts into the mesenchymal stem cells according to claim 2, wherein the TGF-β signal pathway is a type I TGF-β receptors participated pathway, and the cAMP signal pathway is an EPAC/RAP1 signal pathway.

6. The method for inducing the human fibroblasts into the mesenchymal stem cells according to claim 2, wherein
   the pretreatment step comprises pretreating the human fibroblasts for about 4-6 days to obtain a first treated cells; and
   the directional induction comprises:
   directionally inducing the first treated cells for about 6-10 days.

* * * * *